US012499993B2

(12) United States Patent
Matthews

(10) Patent No.: US 12,499,993 B2
(45) Date of Patent: Dec. 16, 2025

(54) SYSTEM AND METHOD OF LASER-ENGRAVING MEDICAL INFORMATION ONTO A MEDICAL OBJECT

(71) Applicant: Keila Matthews, Brooklyn, NY (US)

(72) Inventor: Keila Matthews, Brooklyn, NY (US)

( * ) Notice: Subject to any disclaimer, the term of this patent is extended or adjusted under 35 U.S.C. 154(b) by 270 days.

(21) Appl. No.: 18/356,214

(22) Filed: Jul. 20, 2023

(65) Prior Publication Data

US 2024/0029876 A1 Jan. 25, 2024

Related U.S. Application Data

(60) Provisional application No. 63/368,965, filed on Jul. 20, 2022.

(51) Int. Cl.
*G16H 40/40* (2018.01)
*G16H 10/60* (2018.01)

(52) U.S. Cl.
CPC ............. *G16H 40/40* (2018.01); *G16H 10/60* (2018.01)

(58) Field of Classification Search
CPC ........ G16H 40/40; G16H 10/60; G16H 40/63; G16H 20/10
See application file for complete search history.

(56) References Cited

U.S. PATENT DOCUMENTS 7,006,893 B2 2/2006 Hart
8,109,066 B2 2/2012 Leu
9,073,206 B2 7/2015 Carson
2004/0225528 A1* 11/2004 Brock .................... G06Q 10/10 705/2
2005/0284313 A1* 12/2005 Louviere ................ B41F 17/22 101/35
2009/0171654 A1 7/2009 Spain
2019/0134743 A1 5/2019 Valette

FOREIGN PATENT DOCUMENTS

JP 2003316903 A 11/2003
JP 2004065986 A 3/2004
JP 2015129012 * 7/2015
WO WO2004036479 A2 4/2004

OTHER PUBLICATIONS

Shete, Nikhil Arun et. al. "Changing scenario of packaging in pharmaceutical industry." World Journal of Pharmaceutical Research. 2020: vol. 9, January issue 1 (Year: 2020).*

* cited by examiner

*Primary Examiner* — Linh Giang Le

(57) ABSTRACT

A system used to implement a method of laser-engraving medical information onto a medical object includes at least one computing system and at least one laser-engraving machine. The computing system manages medical information that is associated to a specific medical object. The computing system is communicably coupled to the laser-engraving machine so that the computing system can relay the medical information to the laser engraving machine. The laser-engraving machine then inscribes the medical information as a physical engraving onto a desired external surface of the specific medical object with a laser emitter. The specific medical object is preferably a pill bottle made of a laser-sensitive plastic, and the medical information is preferably a set of dosing instructions for the medicine retained within the pill bottle.

11 Claims, 9 Drawing Sheets

SYSTEM AND METHOD OF LASER-ENGRAVING MEDICAL INFORMATION ONTO A MEDICAL OBJECT

The current application claims a priority to the U.S. provisional patent application Ser. No. 63/368,965 filed on Jul. 20, 2023.

FIELD OF THE INVENTION

The present invention generally relates to pharmaceuticals. More specifically, the present invention relates to laser-engraving a patient's dosing instructions directly onto a medical object such as high-density polyethylene plastic bottles, vials, cartons, blister packs, etc.

BACKGROUND OF THE INVENTION

The current standard is to print a paper label for dosing instructions of a specific medicine and then adhere the paper label onto a bottle, carton, vial, etc. that is retaining the specific medicine. Moreover, the current standard is very slow at bringing pharmaceutical drugs going through a clinical trial to market.

Therefore, an objective of the present invention is to eliminate using ink to print, tooling dyes, manually applying a paper label, and the actual paper used to print the label. Another objective of the present invention is to eliminate the issues of re-ordering a label due to the label accidentally tearing when being applied, labels not sticking to the component due to inadequate adhesive, labels not sticking to the component due to environmental conditions (ambient, refrigerated, frozen), and greatly reducing the cycle time of how quickly the drug gets to the commercial market and to the consumer.

DETAILED DESCRIPTION OF THE INVENTION

All illustrations of the drawings are for the purpose of describing selected versions of the present invention and are not intended to limit the scope of the present invention.

Figure 1:
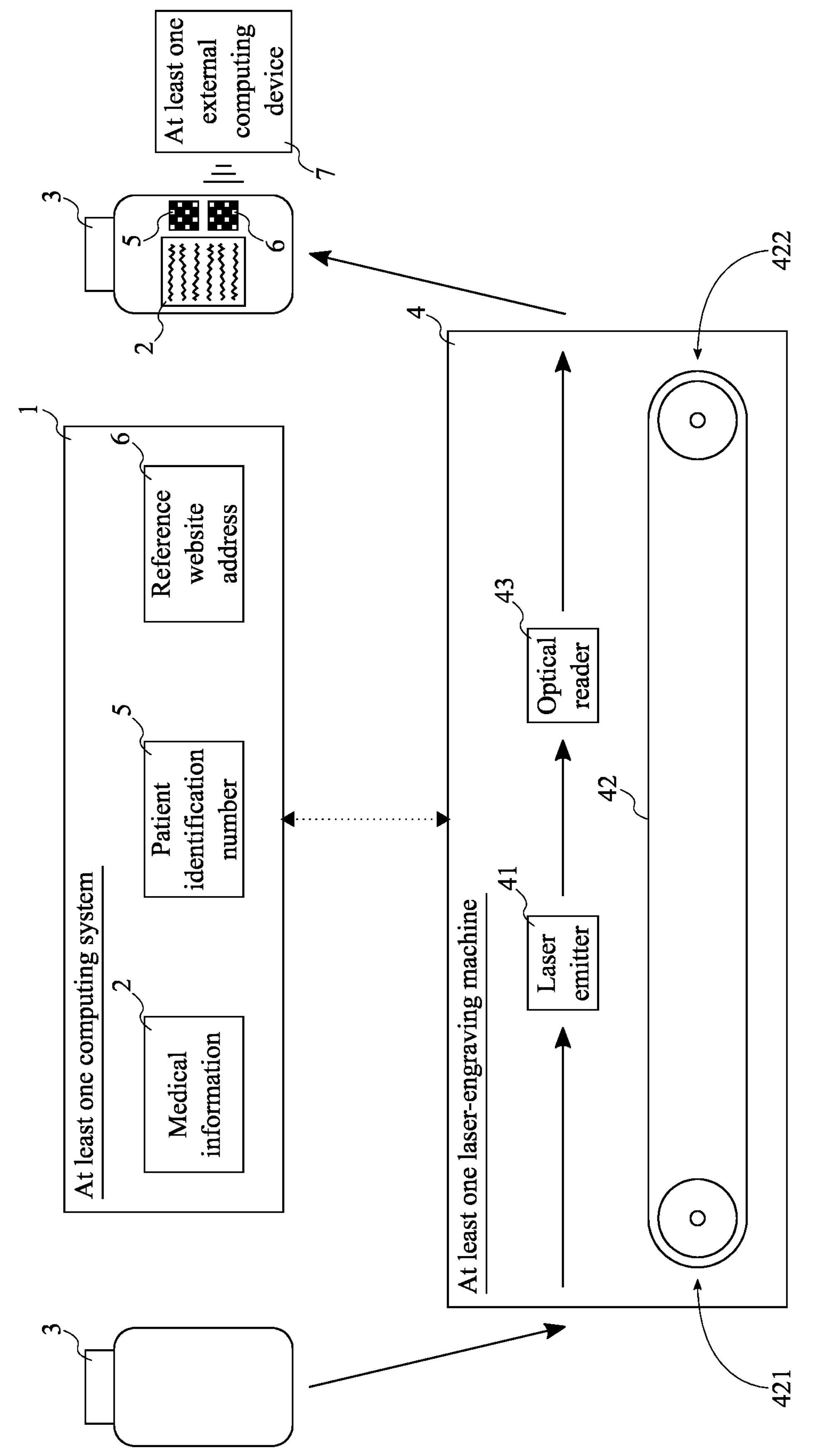
FIG. 1 is a block diagram illustrating the system of the present invention.

The present invention is a system and method of laser-engraving medical information onto a medical object, which reduces the need for consumable items (e.g., paper, ink, tool dyes, etc.) to print medical information onto a medical object. As can be seen in FIG. 1, the system used to implement the method of the present invention is provided with at least one computing system 1 and at least one laser-engraving machine 4. The computing system 1 is used to manage and process data for the present invention and is specifically used to manage medical information 2 that is associated with a specific medical object 3 (Step A). In some embodiments of the present invention, the specific medical object 3 is a medicine container (e.g., a pill bottle, a vial, a carton, etc.) that is preferably made of a laser-sensitive polymer (e.g., high-density polyethylene or another kind of plastic), while the medical information 2 includes a set of dosing instructions. In some other embodiments of the present invention, the specific medical object 3 is a kind of medical component (e.g., a syringe), while the medical information 2 includes a set of usage instructions. The laser-engraving machine 4 is used to selectively remove layers of material from an object in order to create visible markings on the object. The laser-engraving machine 4 is communicably coupled with the computing system 1 (Step B) so that the laser-engraving machine 4 and the computing system 1 can exchange data and/or instructions with each other with a wired or wireless communication connection. In addition, the computing system 1 may be an external device (e.g., a desktop, a laptop, a tablet personal computer, a smartphone, etc.) that is physically separate from the laser-engraving machine 4 or may an internal device that is operatively integrated into the laser-engraving machine 4 as its controller.

Figure 2:
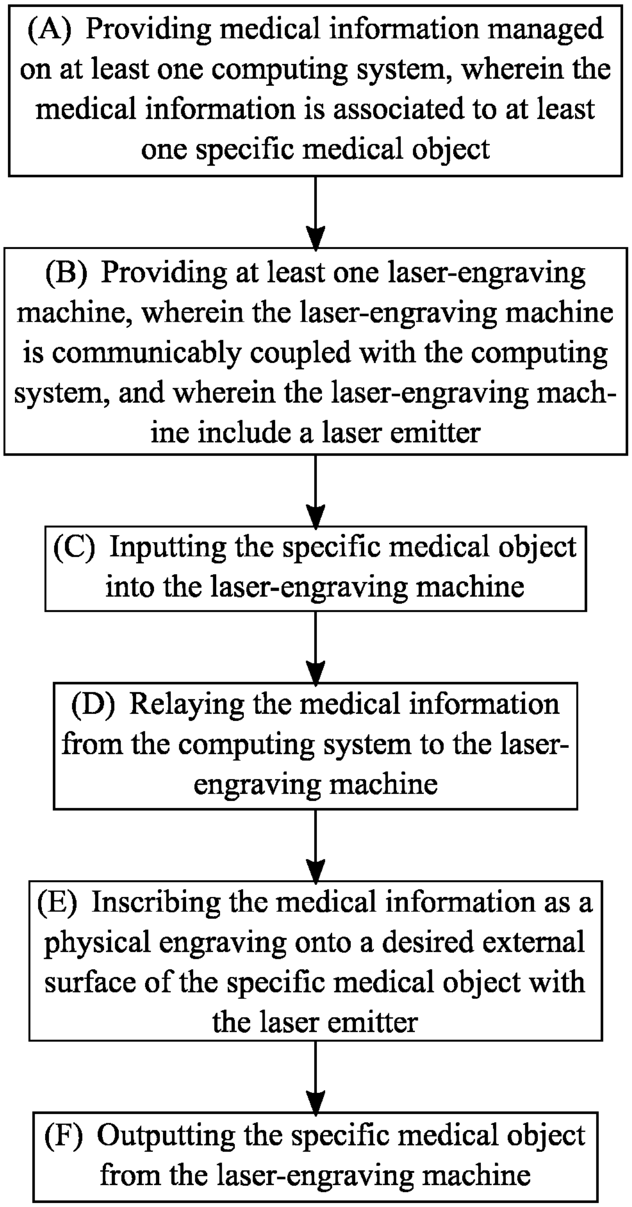
FIG. 2 is a flowchart illustrating an overall process for the method of the present invention.

As can be seen in FIG. 2, an overall process followed by the method of the present invention allows the aforementioned components of the system to manufacture medical objects with laser-engraved medical information. The overall process begins by inputting the specific medical object 3 into the laser-engraving machine 4 (Step C) so that the specific medical object 3 is readily available to be modified by the laser-engraving machine 4. The overall process continues by relaying the medical information 2 from the computing system 1 to the laser-engraving machine 4 (Step D) so that the medical information 2 is readily available to be inscribed by the laser-engraving machine 4. The medical information 2 is then inscribed as a physical engraving onto a desired external surface of the specific medical object 3 with a laser emitter 41 of the laser-engraving machine 4 (Step E), which allows the medical information 2 to be physically visible on the desired external surface of the specific medical object 3. The overall process concludes by outputting the specific medical object 3 from the laser-engraving machine 4 (Step F) so that the specific medical object 3 with its laser-engraved medical information is ready for regular use.

Figure 3:
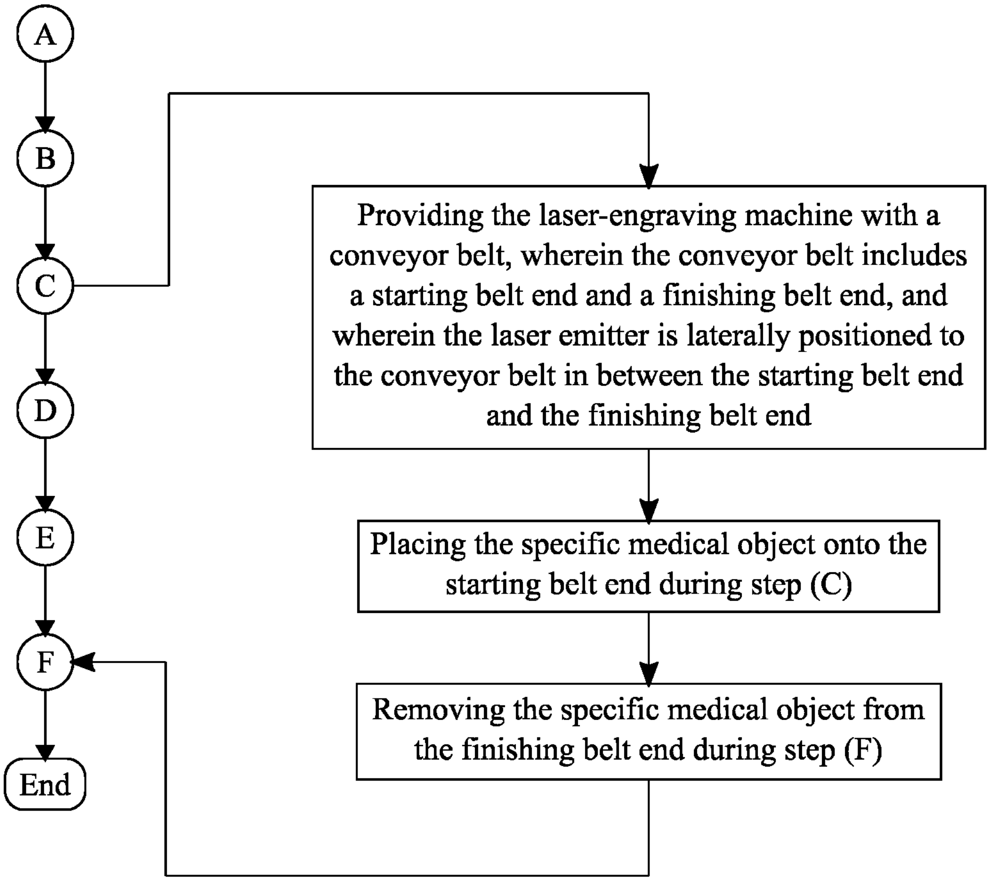
FIG. 3 is a flowchart illustrating a subprocess for moving the specific medical object along a conveyor belt through the laser-engraving machine.

As can be seen in FIG. 3, a subprocess followed by the method of the present invention is used to move the specific medical object 3 through the laser-engraving machine 4. Thus, the laser-engraving machine 4 may be provided with a conveyor belt 42, which includes a starting belt end 421 and a finishing belt end 422. The laser emitter 41 would be laterally positioned to the conveyor belt 42 in between the starting belt end 421 and the finishing belt end 422. The conveyor belt 42 is used to move the specific medical object 3 from the starting belt end 421, past the laser emitter 41, and to the finishing belt end 422. Consequently, this subprocess places the specific medical object 3 onto the starting belt end 421 during Step C and removes the specific medical object 3 from the finishing belt end 422 during Step F.

Figure 4:
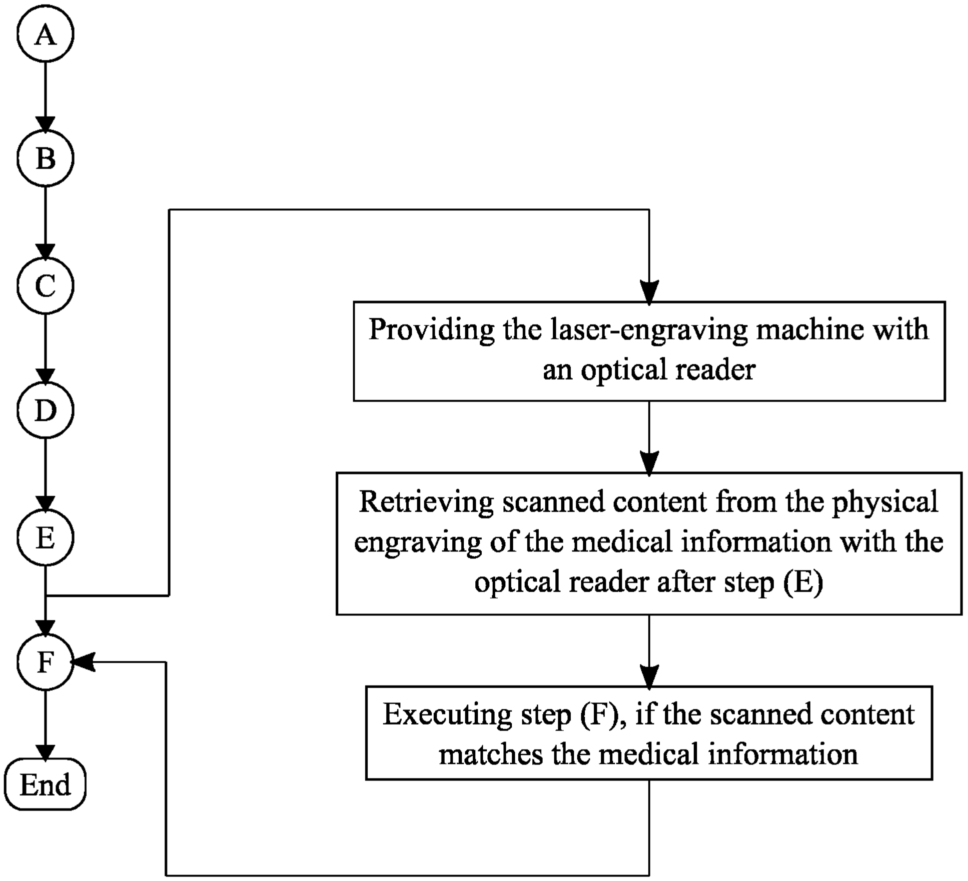
FIG. 4 is a flowchart illustrating a subprocess for verifying the medical information that is laser-engraved onto the specific medical object.

As can be seen in FIG. 4, another subprocess followed by the method of the present invention is used to quality control the laser-engraved medical information 2. Thus, the laser-engraving machine 4 may be provided with an optical reader 43, which is used to scan and image visible markings on a surface. The optical reader 43 would be laterally positioned to the conveyor belt 42 in between the laser emitter 41 and the finishing belt end 422. This subprocess retrieves scanned content from the physical engraving of the medical information 2 with the optical reader 43 after Step E and then executes Step F, if the scanned content matches the medical information 2, as a way to make sure that the physical engraving of the medical information 2 is correct.

Figure 5:
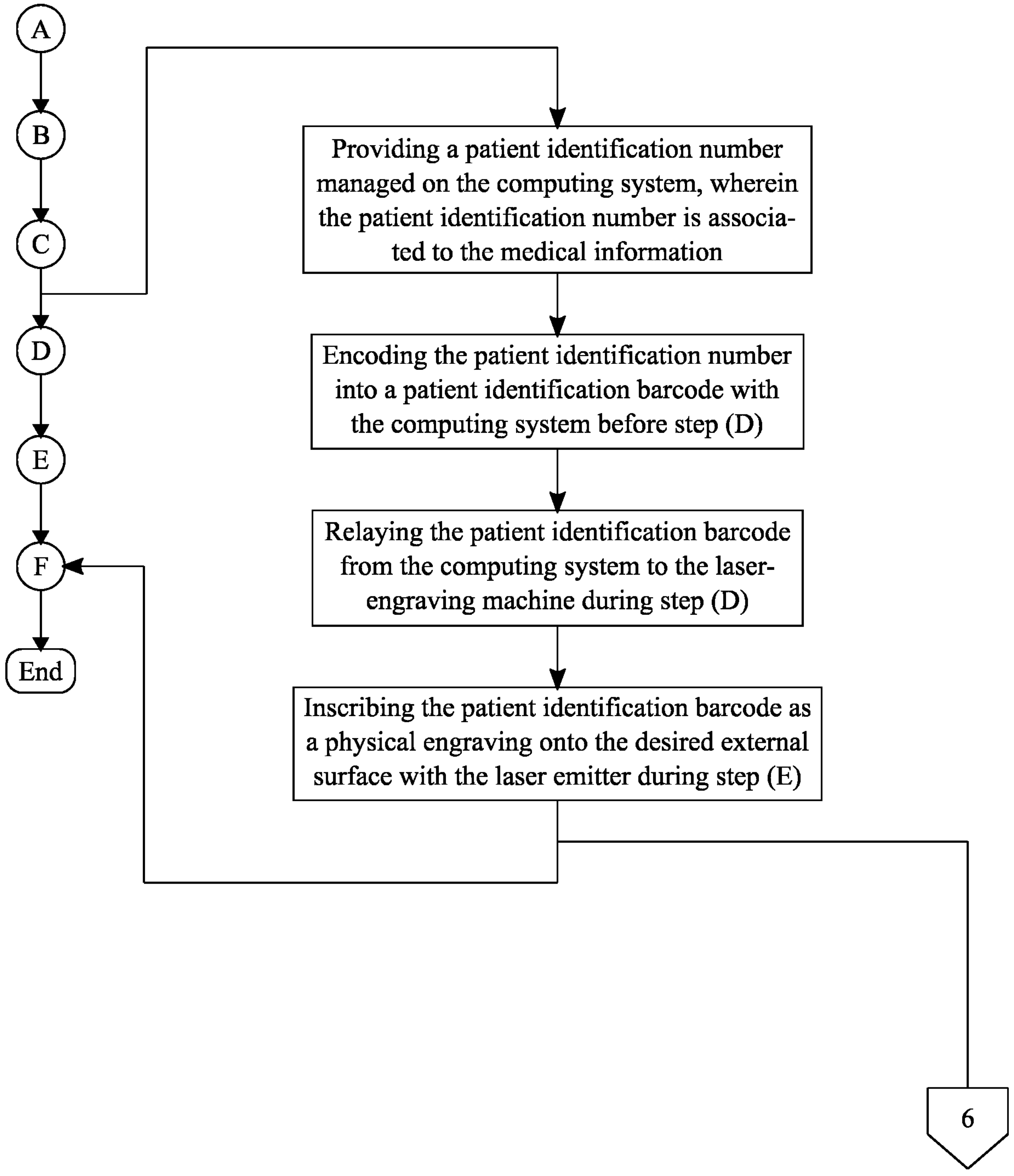
FIG. 5 is a flowchart illustrating a subprocess for encoding a patient identification number onto the specific medical object.

As can be seen in FIG. 5, another subprocess followed by the method of the present invention is used to associate the specific medical object 3 with a specific patient. Thus, the computing system 1 may further manage a patient identification number 5, which is associated to the medical information 2. For example, if the specific medical object 3 is a pill bottle, and if the medical information 2 is a set of dosing instructions, then the patient identification number 5 would associate the pill bottle and the set of dosing instruction with a specific patient. Expanding this example to multiple patients with multiple pill bottles, the patient identification number 5 for each pill bottle can be used to conduct clinical trials on a specific medicine retained within each pill bottle. Moreover, this subprocess begins by encoding the patient identification number 5 into a patient identification barcode with the computing system 1 before Step D because the patient identification barcode is a physical representation of the patient identification number 5 that is more easily engravable and readable into the desired external surface of the specific medical object 3. The patient identification barcode is then relayed from the computing system 1 to the laser-engraving machine 4 during Step D so that the patient identification barcode is readily available to be inscribed by the laser-engraving machine 4. This subprocess concludes by inscribing the patient identification barcode as a physical engraving onto the desired external surface with the laser emitter 41 during Step E, which allows the patient identification barcode to be physically visible on the desired external surface of the specific medical object 3. The physical engraving of the patient identification barcode is preferably positioned adjacent to the physical engraving of the medical information 2 on the desired external surface.

Figure 6:
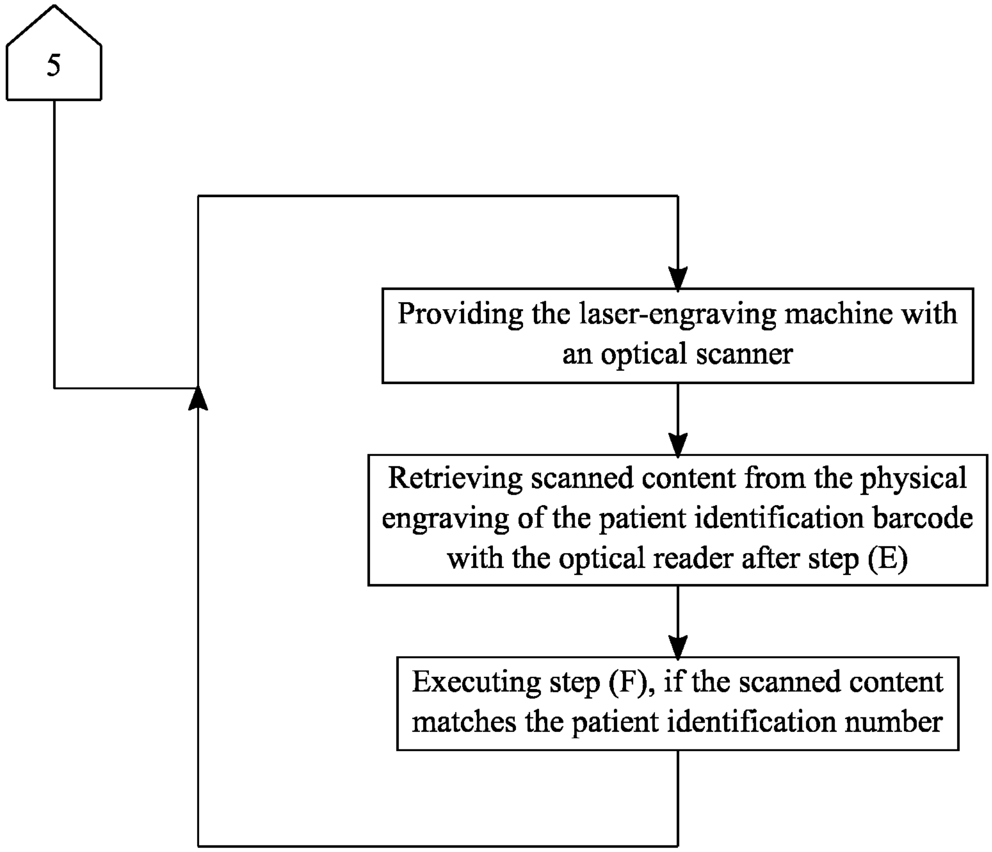
FIG. 6 is a flowchart illustrating a subprocess for verifying the patient identification number that is laser-engraved onto the specific medical object.

As can be seen in FIG. 6, a subprocess related to the patient identification number 5 is used to quality control the laser-engraved patient identification barcode. This subprocess retrieves scanned content from the physical engraving of the patient identification barcode with the optical reader 43 after Step E and then executes Step F, if the scanned content matches the patient identification number 5, as a way to make sure that the physical engraving of the patient identification barcode is correct.

Figure 7:
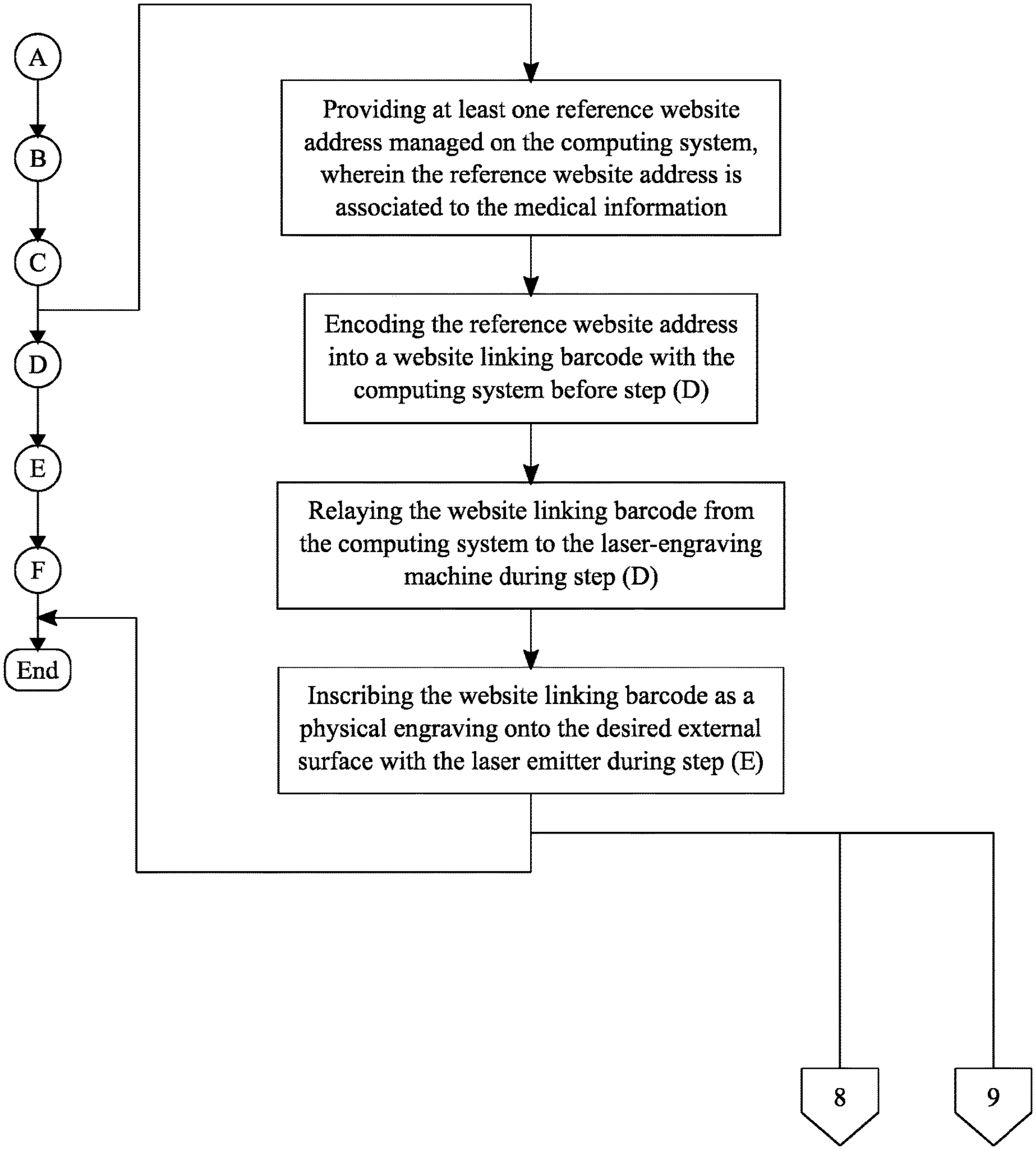
FIG. 7 is a flowchart illustrating a subprocess for encoding a reference website address onto the specific medical object.

As can be seen in FIG. 7, another subprocess followed by the method of the present invention is used to provide supplemental information related to the medical information 2. Thus, the computing system 1 may further manage at least one reference website address 6, which is associated to the medical information 2. The reference website address 6 can be, but is not limited to, a website that provides more detailed information related to the medical information 2, a website that provides more detailed information on any contents of the specific medical object 3, or a website that translates the medical information 2 to a different language. For example, if the specific medical object 3 is a pill bottle, and if the medical information 2 is a set of dosing instructions, then the reference website address 6 could provide more detailed information on the pills retained within the pill bottle (e.g., side effects of the pills, ingredients list of the pills, etc.). Moreover, this subprocess begins by encoding the reference website address 6 into a website linking barcode with the computing system 1 before Step D because the website linking barcode is a physical representation of the reference website address 6 that is more easily engravable and readable into the desired external surface of the specific medical object 3. The website linking barcode is then relayed from the computing system 1 to the laser-engraving machine 4 during Step D so that the website linking barcode is readily available to be inscribed by the laser-engraving machine 4. This subprocess concludes by inscribing the website linking barcode as a physical engraving onto the desired external surface with the laser emitter 41 during Step E, which allows the website linking barcode to be physically visible on the desired external surface of the specific medical object 3. Similar to the patient identification barcode, the physical engraving of the website linking barcode is preferably positioned adjacent to the physical engraving of the medical information 2 on the desired external surface.

Figure 8:
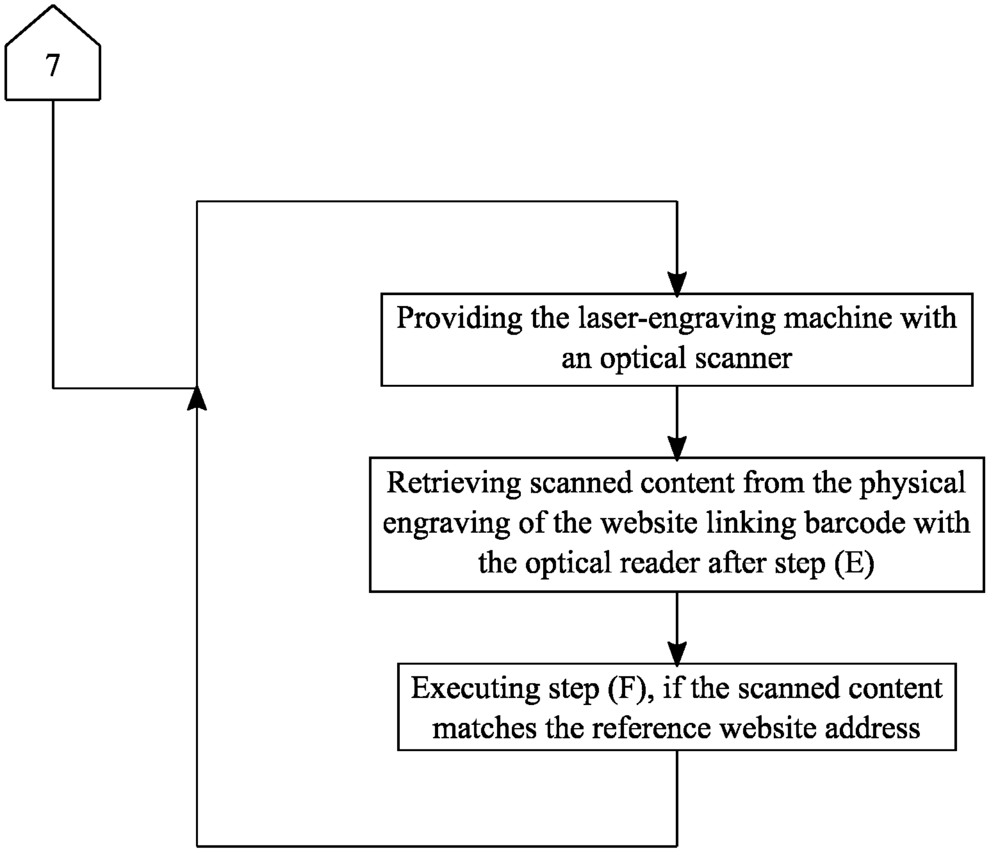
FIG. 8 is a flowchart illustrating a subprocess for verifying the reference website address that is laser-engraved onto the specific medical object.

As can be seen in FIG. 8, a subprocess related to the reference website address 6 is used to quality control the laser-engraved website linking barcode. This subprocess retrieves scanned content from the physical engraving of the website linking barcode with the optical reader 43 after Step E and then executes Step F, if the scanned content matches the reference website address 6, as a way to make sure that the physical engraving of the website linking barcode is correct.

Figure 9:
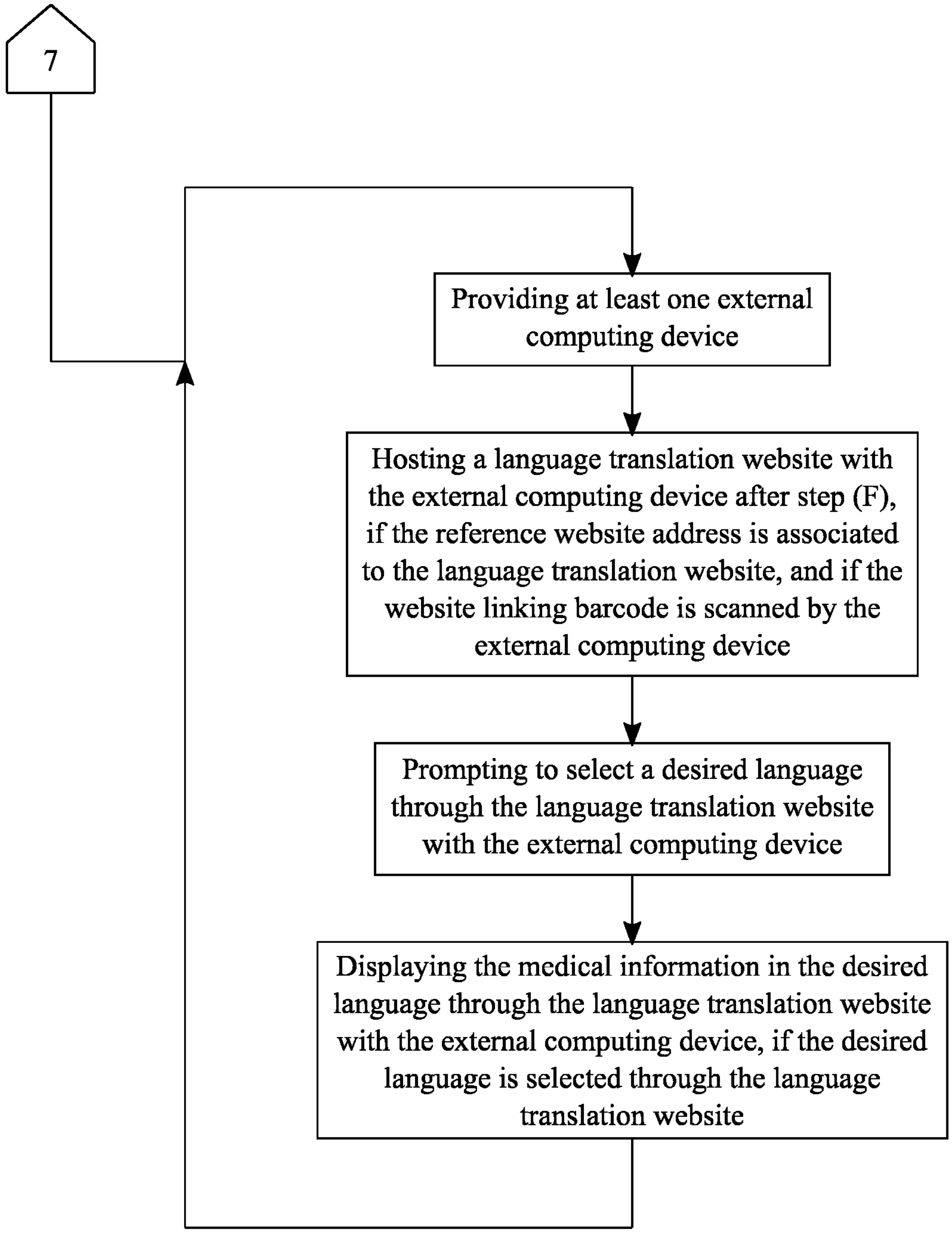
FIG. 9 is a flowchart illustrating a subprocess for using the reference website address to translate the medical information from its original language to a different desired language.

As can be seen in FIG. 9, another subprocess related to the reference website address 6 is used to translate the medical information 2 from its original language to a different language. Thus, a user of the specific medical object 3 is provided with at least one external computing device 7 (e.g., a desktop, a laptop, a tablet personal computer, a smartphone, etc.). This subprocess begins by hosting a language translation website with the external computing device 7 after Step F, if the reference website address 6 is associated to the language translation website, and if the website linking barcode is scanned by the external computing device 7. The language translation website provides a user with translation services for a variety of different languages. The subprocess continues by prompting to select a desired language through the language translation website with the external computing device 7. The language translation website preferably implements a drop-down menu that allows a user to select the desired language for translation of the medical information 2. The subprocess concludes by displaying the medical information 2 in the desired language through the language translation website with the external computing device 7, if the desired language is selected through the language translation website. For example, if the specific medical object 3 is a pill bottle, and if the medical information 2 is a set of dosing instructions, then the reference website address 6 could translate the medical information 2 from English to Spanish so that a Spanishspeaking person would be able to take medication from the pill bottle with English dosing instructions.

Supplemental Description

The present invention is for laser-engraving a set of dosing instructions onto medical components and works by uploading the dosing instructions onto the laser software. Plastic bottles, vials, cartons, syringes, etc. are placed on the conveyor belt. The laser is positioned next to the conveyor belt. Once the component reaches the laser, the laser engraves the dosing instructions directly onto the component along with barcodes.

Once the component is engraved, the component continues down the conveyor, where a vision system scans the dosing instructions and barcodes for 100% accuracy. The barcodes contain the electronic booklet labels, which consist of the dosing instructions translated into different languages, and patient identification numbers, which are obtained from the pharmaceutical companies and are used for the purposes of randomizing patients in clinical trials.

The process works by electronically receiving the patient dosing instructions documentation. The documentation is then uploaded to the laser system software. Then the laser engraves the text directly onto the component. The laser also engraves a number of barcodes. One barcode contains a patient identification number. Another barcode represents the electronic booklet label. The patient then scans the electronic booklet label barcode with the proprietary application software using their cell phone. A drop-down menu of languages then appears. The patient simply picks their preferred language, and the dosing instructions then appears in that language.

The barcodes used in the present invention do not contain the standard barcode information used in the field presently. These barcodes contain patient specific information that is used in clinical trials.

These barcodes are also used on components that are too small to print or engrave any text on such as small vials or syringes. In those cases, a barcode is engraved on the component. The patient then scans the barcode with the proprietary application software using their cell phone, displaying the dosing instructions.

In summary, the difference between the present invention and the prior art is that the present field is still using paper, ink, tool dyes, to put it on a press machine. The present invention eliminates all of those consumables.

Although the invention has been explained in relation to its preferred embodiment, it is to be understood that many other possible modifications and variations can be made without departing from the spirit and scope of the invention as hereinafter claimed.

What is claimed is:

1. A method of laser-engraving medical information onto a medical object, the method comprising the steps of:

(A) providing medical information and at least one reference website address managed on at least one computing system, wherein the medical information is associated to at least one specific medical object, and wherein the reference website address is associated to the medical information;

(B) providing at least one laser-engraving machine, wherein the laser-engraving machine is communicably coupled with the computing system, and wherein the laser-engraving machine includes a laser emitter;

(C) inputting the specific medical object into the laser-engraving machine;

(D) relaying the medical information from the computing system to the laser-engraving machine;

(E) inscribing the medical information as a physical engraving onto a desired external surface of the specific medical object with the laser emitter;

(F) outputting the specific medical object from the laser-engraving machine;

encoding the reference website address into a website linking barcode with the computing system before step (D);

relaying the website linking barcode from the computing system to the laser-engraving machine during step (D); and inscribing the website linking barcode as a physical engraving onto the desired external surface with the laser emitter during step (E).

2. The method as claimed in claim 1, wherein the specific medical object is a medicine container, and wherein the medical information includes a set of dosing instructions.

3. The method as claimed in claim 2, wherein the medicine container is made of a laser-sensitive polymer.

4. The method as claimed in claim 1 further comprising the steps of:

providing the laser-engraving machine with a conveyor belt, wherein the conveyor belt includes a starting belt end and a finishing belt end, and wherein the laser emitter is laterally positioned to the conveyor belt in between the starting belt end and the finishing belt end;

placing the specific medical object onto the starting belt end during step (C); and removing the specific medical object from the finishing belt end during step (F).

5. The method as claimed in claim 1 further comprising the steps of:

providing the laser-engraving machine with an optical reader;

retrieving scanned content from the physical engraving of the medical information with the optical reader after step (E); and executing step (F), if the scanned content matches the medical information.

6. The method as claimed in claim 1 further comprising the steps of:

providing a patient identification number managed on the computing system, wherein the patient identification number is associated to the medical information;

encoding the patient identification number into a patient identification barcode with the computing system before step (D);

relaying the patient identification barcode from the computing system to the laser-engraving machine during step (D); and inscribing the patient identification barcode as a physical engraving onto the desired external surface with the laser emitter during step (E).

7. The method as claimed in claim 6, wherein the physical engraving of the patient identification barcode is positioned adjacent to the physical engraving of the medical information on the desired external surface.

8. The method as claimed in claim 6 further comprising the steps of:

providing the laser-engraving machine with an optical scanner;

retrieving scanned content from the physical engraving of the patient identification barcode with the optical reader after step (E); and executing step (F), if the scanned content matches the patient identification number.

9. The method as claimed in claim 1, wherein the physical engraving of the website linking barcode is positioned adjacent to the physical engraving of the medical information on the desired external surface.

10. The method as claimed in claim 1 further comprising the steps of:

providing the laser-engraving machine with an optical scanner;

retrieving scanned content from the physical engraving of the website linking barcode with the optical reader after step (E); and executing step (F), if the scanned content matches the reference website address.

11. The method as claimed in claim 1 further comprising the steps of:

providing at least one external computing device;

hosting a language translation website with the external computing device after step (F), if the reference website address is associated to the language translation website, and if the website linking barcode is scanned by the external computing device;

prompting to select a desired language through the language translation website with the external computing device; and displaying the medical information in the desired language through the language translation website with the external computing device, if the desired language is selected through the language translation website.

* * * * *